United States Patent
Wang et al.

(10) Patent No.: US 6,187,330 B1
(45) Date of Patent: Feb. 13, 2001

(54) CONTROLLED RELEASE DELIVERY OF PEPTIDE OR PROTEIN

(75) Inventors: Yu-Chang John Wang, Newport Beach; Bing Yang, Redwood City; Robert N. Jennings, Jr., San Jose; Andrew A. Protter, Palo Alto, all of CA (US)

(73) Assignee: Scios Inc., Sunnyvale, CA (US)

( * ) Notice: Under 35 U.S.C. 154(b), the term of this patent shall be extended for 0 days.

(21) Appl. No.: 09/239,410

(22) Filed: Jan. 28, 1999

Related U.S. Application Data

(60) Provisional application No. 60/073,174, filed on Jan. 30, 1998.

(51) Int. Cl.[7] ............................. A61F 2/02; A61K 47/30; A61K 47/32
(52) U.S. Cl. ................... 424/426; 514/772.3; 514/772.6; 514/777
(58) Field of Search ................. 514/772.3, 777, 514/772.6; 424/426

(56) References Cited

U.S. PATENT DOCUMENTS 5,019,400   5/1991   Gombotz et al. .
5,514,566   5/1996   Fiddes et al. .

FOREIGN PATENT DOCUMENTS

| WO 90 13780 | 11/1990 | (WO) . |
| WO 91 16881 | 11/1991 | (WO) . |
| WO 93 10758 | 6/1993 | (WO) . |
| WO 94 05257 | 3/1994 | (WO) . |
| WO 98 43611 | 10/1998 | (WO) . |

*Primary Examiner*—Carlos A. Azpuru
(74) *Attorney, Agent, or Firm*—Knobbe, Martens, Olson & Bear, LLP

(57) ABSTRACT

Compositions and devices for the controlled release delivery of a peptide or protein drug are produced by dispersing a glassy matrix phase comprising the peptide or protein drug and a thermoprotectant in a bioerodable, biocompatible polymer at a temperature that is below the glass transition temperature of the glassy matrix phase and above the melting point of the polymer. The method and composition of the invention may be employed for the local delivery of angiogenic amounts of basic fibroblast growth factor or vascular endothelial growth factor.

36 Claims, 3 Drawing Sheets

CONTROLLED RELEASE DELIVERY OF PEPTIDE OR PROTEIN

CROSS-REFERENCE TO RELATED APPLICATIONS

This is a non-provisional application of co-pending provisional application Ser. No. 60/073,174 filed on Jan. 30, 1998, the disclosure of which is hereby incorporated by reference and to which application priority is claimed under 35 USC 119.

BACKGROUND

This invention relates to the field of controlled delivery of peptides or proteins and to compositions useful for the controlled delivery of peptides or proteins.

Polymeric matrices, typically in the form of microspheres, rods, sheets or pellets, have been employed for the sustained or controlled release of drug products. A variety of techniques are known by which active agents can be incorporated into polymer matrices. Examples are solvent evaporation, spray drying, emulsification, or by simple physical mixing of particles of discrete size or shape. None of these approaches can easily be adapted to the incorporation of peptide or protein drugs into polymers due to the delicate nature of peptides and proteins. Peptides and proteins are susceptible to denaturation by solvents, by emulsification or by heat. In order to avoid the instability problem, U.S. Pat. No. 5,019,400 describes a very low temperature casting process for incorporating proteins into controlled release polymer matrices. This technique has several drawbacks, inasmuch as low temperature processing can be very cumbersome, special equipment is needed and moisture condensation during the process represents a potential problem.

It would be desirable to be able to mix the peptide or protein drug into a molten polymer, which could be cast into a defined shape and size. Unfortunately, most proteins denature at a temperature far below the melting point of polymers.

It is also desirable that the peptide or protein drug be stable under the conditions in which it is released from the polymeric matrix within the body. Most bioerodable polymers are depolymerized within the body by the hydrolysis of ester bonds. This hydrolysis can result in local regions of high acidity. Since many peptide or protein drugs are unstable in acidic conditions, this can result in deactivation of the drug before it is released. One such protein drug, which is unstable under acidic conditions, is basic fibroblast growth factor (bFGF). This protein, which has been isolated in forms varying in length, e.g. 146, 154 and 157 amino acid forms, is a potent angiogenic agent as well as a stimulator of cell proliferation and migration during wound healing. The DNA sequence encoding human bFGF and its deduced amino acid sequence are disclosed in U.S. Pat. No. 5,514,566. Because of its angiogenic properties, it is useful in promoting the local growth of new capillary vascular beds in order to bypass blockages in arteries of individuals having atherosclerotic conditions such as coronary artery disease and peripheral vascular disease. This protein is also chemotactic for fibroblasts, which are the chief cells involved in releasing a matrix required for wound healing, including collagen which determines the tensile strength of the healed wounds. In order to deliver bFGF effectively to a desired site and avoid any potential side effects associated with systemic delivery of bFGF in treating such conditions, it would be desirable to provide a controlled release device for implantation at or near the site at which the angiogenic or wound healing activity is required.

SUMMARY OF THE INVENTION

The present invention provides methods and compositions for the controlled release of peptide or protein drugs and methods for the production of compositions and devices useful for the controlled release of peptide or protein drugs.

In one embodiment of the invention, there is provided a composition for the controlled release of a peptide or protein comprising a biocompatible, bioerodable polymer having dispersed therein a glassy matrix phase comprising the peptide or protein and a thermoprotectant, said glassy matrix phase having a glass transition temperature above the melting point of the polymer. Since the peptide or protein drug is stable within the composition, it can conveniently be formed, in its melt stage, into suitably shaped devices to be used as drug delivery implants, e.g. in the form of rods, films, beads or other desired shapes.

In another embodiment of the invention, there is provided a method of controlled release administration of a bioactive peptide or protein to an animal in need of such administration which comprises implanting a device formed from the composition of this invention into such animal.

In yet another embodiment of the invention, there is provided a method for producing a composition for the controlled release delivery of a bioactive peptide or protein which comprises:

(a) dispersing a glassy matrix comprising the bioactive peptide or protein and a thermoprotectant in a biocompatible, bioerodable polymer at a temperature above the melting point of the polymer and below the glass transition temperature of the glassy matrix; and (b) cooling the dispersion to a temperature at which the polymer is a solid. If desired, the dispersion can be formed or cast into a delivery device having a desired shape prior to cooling.

In preferred embodiments of the invention, the thermoprotectant is selected from the groups consisting of trehalose, melezitose, cellobiose, melibiose, raffinose and lactose. A preferred polymer for use in the compositions and devices of the invention is poly(ε-caprolactone) having a melting point below about 65° C.

The compositions and devices of the invention provide excellent controlled release of bFGF, or vascular endothelial growth factor (VEGF), without significant degradation of the protein, either during the manufacture or delivery of the protein in vivo.

DETAILED DESCRIPTION OF THE INVENTION

Figure 1:
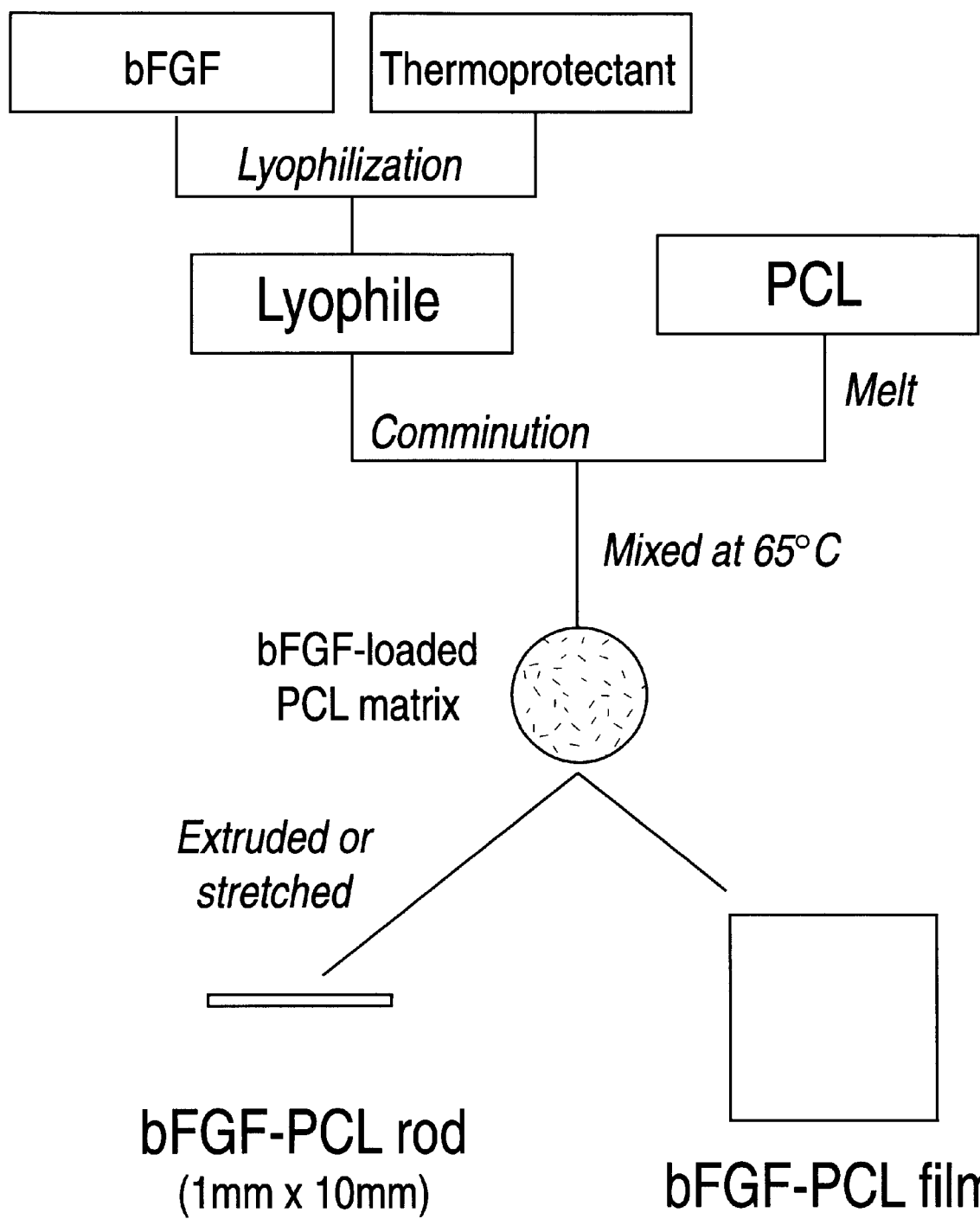
FIG. 1 is a schematic representation of an embodiment of the method of the invention for preparing a controlled release device for the delivery of bFGF.

In accordance with the present invention, there is provided an efficient means for producing compositions and devices for the controlled release delivery of peptide or protein drugs. We have determined that peptide or protein drugs can be dispersed in bioerodable, biodegradable polymer matrices in the melt stage, provided the peptide or protein drug is dispersed in a glassy matrix phase having a glass transition temperature that is higher than the melting point of the polymer. The method of this invention for producing a particular controlled release delivery device is illustrated in FIG. 1. This figure is a schematic representation of the production of a controlled release device for the delivery of bFGF utilizing poly(ε-caprolactone) as the polymer.

The method and composition of the invention is advantageously employed for the controlled release delivery of any protein or peptide drug which is susceptible to inactivation by heat. Generally any protein or peptide drug which relies for its activity on maintenance of its tertiary structure will be susceptible to inactivation by heating. While some small peptides may not require maintenance of tertiary structure for activity, almost all protein drugs are susceptible to inactivation by heating. Thus, the method and composition of the invention may employ a wide variety of proteins, including, for example, growth factors, hematopoietic factors, hormones, cytokines, lymphokines and factors which stimulate or suppress immune function. We have found the methods and composition of the invention to be particularly well suited for the local delivery of human bFGF and vascular endothelial growth factor (VEGF).

The glassy matrix phase can be produced by lyophilizing an aqueous solution of the peptide or protein drug and a suitable thermoprotectant. The particular thermoprotectant selected and its concentration relative to the peptide or protein will determine the precise glass transition temperature of the lyophile. Generally, the weight ratio of thermoprotectant to peptide or protein drug is between about 2 and 200. One skilled in the art will be able to determine the required glass transition temperature of any combination. Glass transition is defined as the reversible change in an amorphous material from (or to) a viscous rubbery state to (or from) a hard and relatively brittle one (American Society for Testing and Materials (ASTM) E 1142). Glass transition temperature (Tg) is defined as the approximate midpoint of the temperature range at which the glass transition takes place (ASTM D 4092). The glass transition temperature of the glassy matrix phase containing the peptide or protein drug and the thermoprotectant can be determined by a variety of techniques, the most popular of which is differential scanning calorimetry (DSC). If a glassy material is heated at a constant rate, a baseline shift can be found in the relation of heat flow and its temperature. The temperature corresponding to the midpoint of the two baselines is considered the glass transition temperature.

Trehalose, melezitose, lactose, maltose, cellobiose, melibiose and raffinose are preferred thermoprotectants. Since moisture affects the Tg of the glassy matrix phase, the moisture content of the glassy matrix phase is preferably less than 1%, more preferably less than 0.5%. This is particularly true if one desires to use sucrose as the thermoprotectant, since excess moisture can cause the Tg of the sucrose-containing matrix to drop below the melting point of the preferred polymer, poly(ε-caprolactone). We employed TA 2910 and TA 2920 differential scanning calorimeters to determine the Tg for various lyophilized matrices containing bFGF. Approximately 5 mg of each sample was weighed and hermetically sealed in an aluminum pan with a crimping press. DSC data were collected in the heating mode at a heating rate of 10° C./min. Before beginning the temperature ramp, the sample was isothermally equilibrated for 5 minutes at a temperature of 30° C. or more below the expected Tg before beginning the experiment. Where the glass transition was associated with enthalpic relaxation, samples were heated past Tg, cooled to the starting temperature and reheated to measure Tg in the second scan. Table 1, below, indicates the glass transition temperatures for lyophiles of bFGF with various excipients.

TABLE 1

Glass Transition Temperature of bFGF Lyophiles

| Formulation | Excipient | Excipient (%) (prior to freeze drying) | bFGF (mg/vial) | Moisture (%) | Tg (° C.) |
| --- | --- | --- | --- | --- | --- |
| 1 | Lactose | 4.02 | 13.43 | 0.82 | 85.8 |
| 2 | Maltose | 4.01 | 13.55 | 0.94 | 80.1 |
| 3 | Cellobiose | 4.02 | 13.48 | 0.88 | 82.2 |
| 4 | Melezitose | 4.02 | 13.70 | 0.84 | 84.4 |
| 5 | Trehalose | 4.00 | 13.82 | 0.93 | 84.3 |
| 6 | Melibiose | 4.02 | 14.12 | 1.33 | 76.5 |
| 7 | Raffinose | 4.01 | 13.40 | 0.98 | 92.9 |
| 8 | Lactulose | 4.00 | 13.29 | 1.10 | 68.9 |
| 9 | Sodium Gluconate | 4.02 | 14.81 | 2.96 | 51.2 |
| 10 | Sodium Gluconate | 1.99 | 15.45 | 3.18 | 52.1 |
| 11 | Sucrose | 4.03 | 13.95 | 0.84 | 61.7 |
| 12 | Sucrose | 9.00 | 9.25 | 1.38 | 56.5 |

In addition to the peptide or protein drug, the glassy matrix phase may also contain other conventional pharmaceutical excipients in the usual effective concentrations. Typically employed excipients include, for example, wetting agents, disintegrants, surfactants, buffer salts, preservatives (antibacterials), antioxidants and chelating agents. As is known in the art, one may particularly want to employ an anti-aggregant as an excipient, since concentrations of peptide or protein drug are relatively high in controlled release devices and aggregation of peptide or protein may occur in the absence of such an excipient. Effective anti-aggregants are well known to those skilled in the art, as are the concentrations at which they are conventionally employed. They include, for example, polyols such as inositol, xylitol, mannitol, maltose, arabinose and galactose.

Lyophilization of the aqueous solution containing the thermoprotectant, peptide or protein drug and other excipients, if any, is carried out using techniques well known in the pharmaceutical field (see, e.g., Remington's Pharmaceutical Sciences, 17$^{th}$ Ed., p. 1538). Lyophilization produces a glassy matrix phase in the form of a powder or a cake which may be comminuted to produce a powder suitable for dispersion in the polymer.

The glassy matrix phase containing the peptide or protein drug is then dispersed in a bioerodable, biocompatible polymer which has a melting point below the glass transition temperature of the glassy matrix phase. As used herein, the term "bioerodable" means that the polymer is sufficiently degradable in a physiological environment to allow the controlled release of the peptide or protein drug. The term "biocompatible" means that the degradation products of the polymer are non-toxic and do not inactivate the peptide or protein drug. Preferably, the polymer is also biodegradable, i.e. it is completely degraded and resorbed in a physiological environment, so that it is unnecessary to physically remove any remaining components of the device after it has delivered the drug.

A preferred polymer for use in the compositions of the invention is poly(ε-caprolactone). More preferably, the poly (ε-caprolactone) employed in the compositions of the invention has a molecular weight between about 2,000 and 30,000, most preferably between about 10,000 and 20,000. Poly(ε-caprolactone) in this range of molecular weight has a melting point of about 59–65° C. Poly(ε-caprolactone) is also a highly desirable polymer when the peptide or protein drug being delivered is one which is not acid stable, e.g. bFGF. The rate of hydrolysis of poly(ε-caprolactone) under physiological conditions is sufficiently slow that degradation of the polymer does not result in local regions of low pH which would inactivate the peptide or protein. This is particularly important, for example, when releasing bFGF, since the protein is completely inactivated at pH 3–4 in about 20–30 minutes. The preferred thermoprotectants of the invention may also act as porocigens which help to control the release of the peptide or protein drug as they dissolve in the water present in the physiological environment.

Referring again to FIG. 1, the lyophile containing the thermoprotectant, the peptide or protein drug, and/or any other excipients one desires to include are dispersed in the polymer. The polymer is heated to its melting point. In the case of poly(ε-caprolactone) the polymer is heated to about 65° C. The glassy matrix phase is dispersed in the melted polymer using any convenient mixing means. It may be advantageous to disperse additional additives in the polymer to control the drug release rates of the device. In particular, art-known porocigens can be incorporated into the polymer to control the rate of release of the drug. Known porocigens include, for example, sugars, amino acids, mannitol, sorbitol, xylitol and polyethylene glycol. These can be incorporated into the polymer in known effective amounts.

The glassy matrix phase will normally be present in an amount from about 5% to about 25% of the total weight of the composition, preferably from about 10% to about 20% thereof. The precise amount of glassy matrix phase present in the composition will be dictated largely by the concentration of peptide or protein drug contained in the glassy matrix phase, the desired release rate, the size of the device one wishes to implant and the dosage of drug which one desires to deliver to a local site.

As shown in FIG. 1, the polymer containing the glassy matrix phase can be formed into an appropriate shape for use as an implant, e.g. rods, discs, sheets, spheres, prior to cooling. Alternatively, since the peptide or protein is stable within the composition, it can be reheated and formed into a desired shape at a later time.

The drug delivery device of the invention can be implanted into an animal in need of controlled release delivery of the peptide or protein drug in a conventional manner. In the case of a device containing bFGF or VEGF, the device is advantageously implanted at or near the site of a vascular blockage or vascular injury. In this manner, for example, one can treat an animal, e.g. a mammal such as a human, suffering from peripheral vascular disease or coronary artery disease. As the bFGF is released, it promotes angiogenesis which results in the formation of new capillary vessels to carry blood past the site of blockage. Typically, a device for use in such an application will contain from about 25 μg to about 250 μg of bFGF. In experiments in vivo a sufficient amount of bFGF was released in a five day period to promote angiogenesis. The drug delivery device of the invention can also be employed to deliver bFGF to promote wound healing, for example, in the treatment of pressure sores, diabetic ulcers, incision wounds resulting from surgery and/or accidental trauma and the like or in the healing of bone tissue. For such uses, the device may be formed into an appropriate size and shape to be inserted into the wound site. Alternatively, the composition of the invention may be milled into a powder form, which can be applied to the wound site. In such cases, the appropriate dosages are those which will promote angiogenesis in the wound bed and, thereby promote healing. Appropriate dosages will be able to be determined by those skilled in the art and will be dictated at least in part by the nature and size of the wound being treated.

The following non-limiting examples are intended to further illustrate the invention which has been described herein.

EXAMPLE 1

Preparation of bFGF-PCL Rods

A. Preparation of Glassy Matrix Phase 4.42 g of trehalose dihydrate was placed in a 100 mL volumetric flask. 84 mL of 8.37 mg/mL aqueous solution of recombinant human bFGF (154-amino acid form) was added to the flask. The solution was brought to 100 mL with water and then filtered through a 0.2 μm sterile Arodisc® 13 filter (Gelman Science). The filtered solution was then placed in vials (2 mL/vial) for lyophilization.

The aliquots in each vial were first frozen by maintaining the shelf temperature at −45° C. for 2 hours, followed by an annealing step at −10° C. for 2 hours and cooled to −40° C. for an additional 3 hours. Primary drying was performed at −20° C. and −25° C. for 5 and 15 hours, respectively, at 60 mTorr. Secondary drying was performed at 25–30° C. for 10 hrs at 60 mTorr.

B. Incorporation of bFGF Lyophile into PCL 1.192 g of commercially obtained poly(ε-caprolactone) (MW 10,000–20,000) were placed in a sterilized beaker in an oil bath. The oil bath was heated to 90° C. for one hour and then cooled to 65° C. The bFGF lyophile from one vial, produced as described above, was added to the melted PCL. The lyophile was suspended in the viscous PCL and agitated to obtain a homogeneous dispersion.

C. Preparation of bFGF-PCL Rod

The bFGF lyophile-PCL mixture was stretched using a 16 G sterile needle to form a rod of approximately 1 mm diameter. The rod was cooled to room temperature and cut into 10 mm sections.

EXAMPLE 2

Preparation of bFGF-PCL Rods bFGF-PCL rods were prepared in a manner similar to that described in Example 1 using different loadings of bFGF and different thermoprotectant materials. In each case, 2 mL of an aqueous solution containing bFGF (2 mg for low dosage and 50 mg for high dosage), thermoprotectant (80 mg to 370 mg), 20 mM citrate buffer and 1 mM EDTA were filled into each vial for lyophilization. Thermoprotectants employed were trehalose, melezitose and sucrose. These solutions were lyophilized, dispersed in melted PCL and formed into rods in the manner described in Example 1. In the case of the sucrose-containing solution, lyophilization was carried out to a moisture content of 0.5% in order to assure that the Tg of the lyophile was above the melting point of the PCL.

EXAMPLE 3

In Vitro Release of bFGF from Rods

PCL rods (1 mm×10 mm) containing bFGF were prepared in a manner similar to that described in Example 1 using trehalose, melezitose or sucrose as the thermoprotectant. In the case of trehalose and melezitose, the lyophile used to prepare the rods contained a 4% concentration of the thermoprotectant (w/w prior to lyophilization) and the lyophile was dispersed in the PCL at a concentration of 8.3% (w/w). In the case of sucrose, the lyphile used to prepare the rods contained a 9% sucrose concentration (w/w prior to lyophilization) and the lyophile was dispersed in the PCL at a concentration of 13.8% (w/w).

Figure 2:
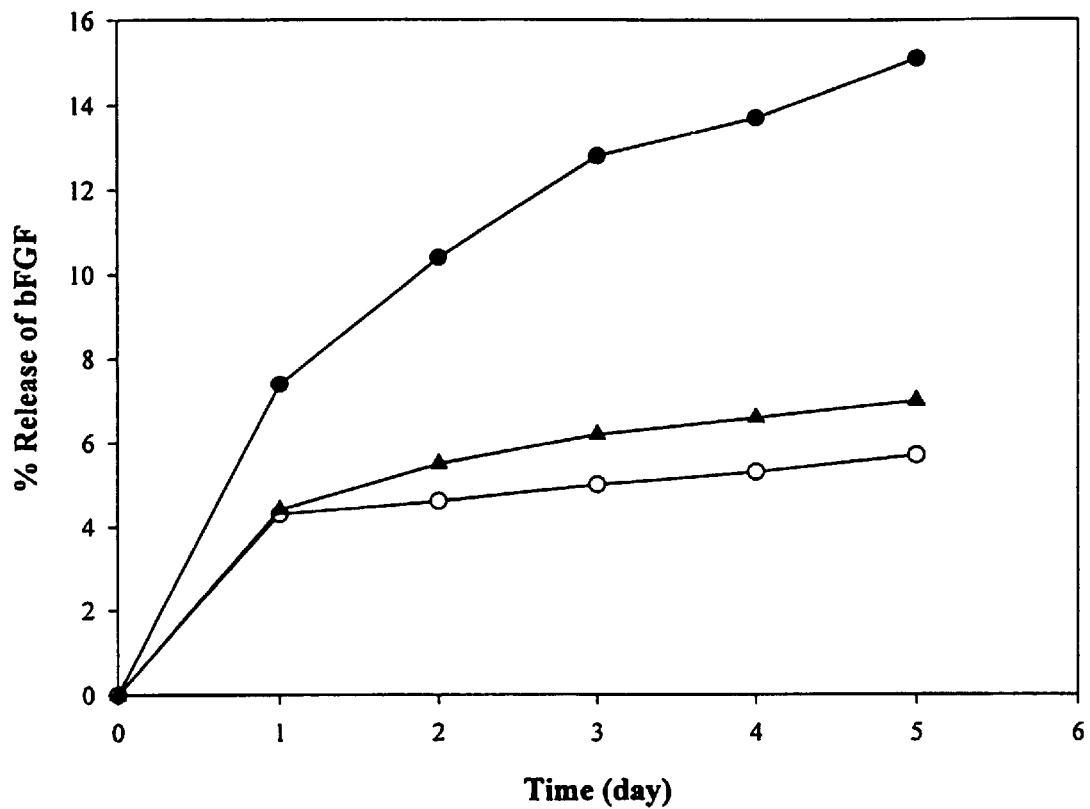
FIG. 2 is a graph which plots the in vitro release of bFGF from three formulations of the invention.

Measurement of in vitro release of the bFGF from the rods was determined at 5° C. The rods were placed in 1 mL of phosphate buffered saline (PBS) solution and the solution was stirred with a stirring bar. The PBS solution was withdrawn at one-day intervals and replaced by fresh PBS solution to maintain volume. Ion-exchange HPLC was used to quantitate the bFGF in the withdrawn PBS solution and the accumulated bFGF released from the rods calculated. Release of the bFGF from the rods over time is plotted in the graph in FIG. 2. In the figure, data points for the trehalose-containing formulation are represented by blank circles; data points for the melezitose-containing formulation are represented by solid triangles; and data points for the sucrose-containing formulation are represented by solid circles.

EXAMPLE 4

Promotion of Angiogenesis by bFGF-PCL Implant

Male and female Sprague Dawley rats (225–425 g body weight) were briefly anesthetized by inhalation of isoflurane. The abdominal area was shaved and cleaned with 70% ethanol. Rods (1 mm×10 mm) containing bFGF (recombinantly produced human bFGF, 154 amino-acid form) in PCL, produced as described in Example 1, were inserted into a 14 gauge intravenous catheter placement needle. The abdominal skin was grasped with tissue forceps and pierced with the needle along the midline approximately 2 cm above the pelvis. The pellet was advanced to a position between the skin and abdominal muscle layers using a fine wire. The needle was removed, animals were weighed and returned to the appropriate cage. Animals were alert and mobile almost immediately after inhalation of isoflurane was discontinued.

Five days after initial placement of bFGF-PCL rods, animals were euthanized by carbon dioxide inhalation or phenobarbital overdose. Body weight was recorded and the abdominal skin was gently incised and reflected to expose the abdominal muscle. Comments regarding location and vascularity and granulation tissue accumulation were recorded and a photograph was taken of each animal. The abdominal muscle layer was removed and placed in 10% buffered formalin. Tissue samples were sectioned at 5 mm intervals and stained with hematoxylin and eosin.

The following formulations were tested for their ability to promote angiogenesis:
Controls
1. bFGF in saline (injected s.c.), 70 µg bFGF in 0.5 ml volume of sterile isotonic saline
2. PCL rod: 9% sucrose lyophile, ratio of lyophile to PCL=0.16
3. PCL rod: 4% trehalose lyophile, ratio of lyophile to PCL=0.09
bFGF-PCL Rods
1. bFGF in 9% sucrose lyophile, ratio of lyophile to PCL=0.17. bFGF load=100 µg/rod
2. bFGF in 4% trehalose lyophile, ratio of lyophile to PCL=0.09. bFGF load=25 µg/rod
3. bFGF in 4% trehalose lyophile, ratio of lyophile to PCL=0.09. bFGF load=100 µg/rod
4. bFGF in 4% melezitose lyophile, ratio of lyophile to PCL=0.09. bFGF load=100 µg/rod Visual inspection of the subcutaneous region containing the rods showed that when bFGF was included in the formulation there was an accumulation of tissue around the rod and the tissue demonstrated a vascularized appearance. When bFGF was not included in the formulation local tissue accumulation was either very slight or absent. When bFGF was administered in saline without the rod formulation there was no obvious effect on subcutanous tissue in the injection region. The effects of bFGF in the rod formulations were dependent on the loading of bFGF for the potency of their actions.

Histological analysis of the tissues showed that when bFGF was included in the formulation there was an accumulation of fibroblasts and blood vessels around the rod. When bFGF was not included in the formulation fibroblast and blood vessel accumulation was either very slight or absent. The fibroblast and blood vessel accumulation seen with bFGF in the rod formulations would be beneficial for wound healing and to stimulate the development of collateral blood vessels in tissue in cases of vascular insufficiency (e.g., peripheral vascular disease or ischemic heart disease).

EXAMPLE 5

Preparation of VEGF-PCL Rods and Bioactivity of VEGF Recovered from the Rods

VEGF-PCL rods were prepared in a manner similar to that described in Example 1 and Example 2 using VEGF as the drug and sucrose as the thermoprotectant. In the preparation, 2 mL of an aqueous solution was lyophilized. The solution contains 6.8 mg of VEGF, 80 mg of sucrose, 20 mM citrate buffer and 1 mM EDTA. The lyophilized cake was then dispersed in melted PCL and formed into VEGF-PCL rods in the manner described in Example 1. The weight ratio of lyophile to PCL was controlled between 0.07 and 0.17.

Figure 3:
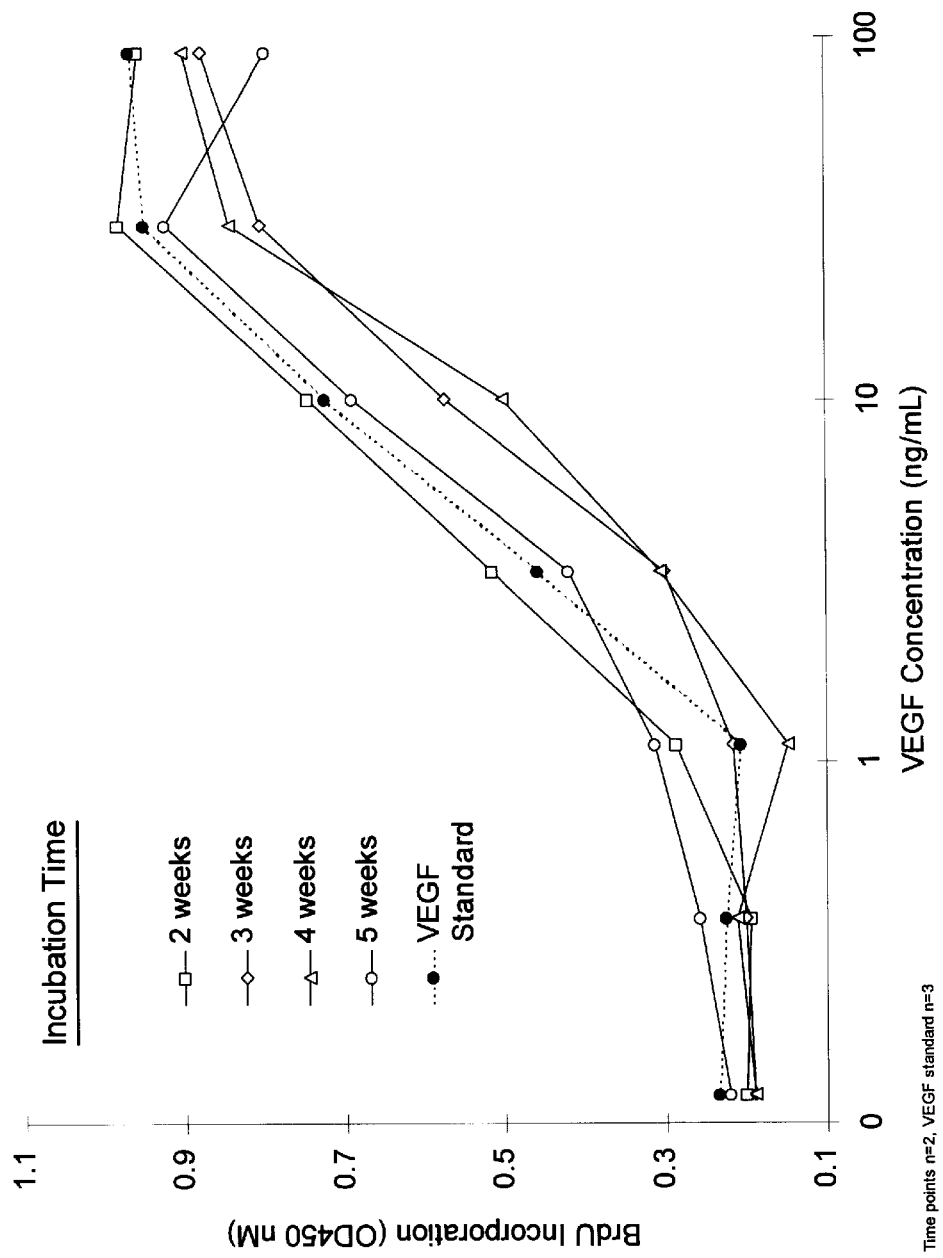
FIG. 3 is a graph which plots the long term in vitro bioactivity of VEGF recovered from polycaprolactone rods.

The bioactivity of VEGF recovered from the rods was determined. The VEGF-PCL rods were incubated in a PBS buffer solution containing 0.1% protease free BSA and 10 µ/mL gentamycin at 37° C. At each time point, the PCL rods were removed out from the solution and placed into a fresh solution with the same composition. The removed solution was analyzed using a bioassay method and the results are plotted in FIG. 3. The in vitro results indicate VEGF is active in the rod after 5 weeks incubation.

The promotion of angiogenesis of the VEGF-PCL rods on Sprague Dawley rats was tested in a manner similar to Example 4. Visual inspection and histological analysis of the subcutaneous region containing the VEGF-PCL rods showed there was an accumulation of tissue around the rod and the tissue demonstrated a vascularized appearance. When VEGF was not included in the formulation, local tissue accumulation was absent.

What is claimed is:

1. A composition for the controlled release of a peptide or protein comprising a biocompatible, bioerodable polymer having dispersed therein a glassy matrix phase comprising the peptide or protein and a thermoprotectant, said glassy matrix phase having a glass transition temperature above the melting point of the polymer.

2. A composition as claimed in claim 1, wherein the biocompatible, bioerodable polymer is biodegradable.

3. A composition as claimed in claim 1, wherein the glass transition temperature of the glassy matrix phase is above 65° C.

4. A composition as claimed in claim 1, wherein the thermoprotectant is selected from the group consisting of trehalose, lactose, maltose, cellobiose, melezitose, melibiose, raffinose and sucrose.

5. A composition as claimed in claim 1, wherein the biocompatible, bioerodable polymer is polycaprolactone.

6. A composition as claimed in claim 1, wherein the biocompatible, bioerodable polymer is poly($\epsilon$-caprolactone) having a melting point below 65° C.

7. A composition as claimed in claim 1, wherein the bioactive peptide or protein is basic fibroblast growth factor or vascular endothelial growth factor.

8. A composition as claimed in claim 7, wherein the thermoprotectant is selected from the group consisting of trehalose, lactose, maltose, cellobiose, melezitose, melibiose, raffinose and sucorse.

9. A composition as claimed in claim 8, wherein the thermoprotectant is sucrose and the glassy matrix phase has a moisture content below 1%.

10. A composition as claimed in claim 8, wherein the thermoprotectant is trehalose.

11. A composition as claimed in claim 7, wherein the biocompatible, bioerodable polymer is poly($\epsilon$-caprolactone).

12. A composition as claimed in claim 8, wherein the biocompatible, bioerodable polymer is poly($\epsilon$-caprolactone).

13. A composition as claimed in claim 9, wherein the biocompatible, bioerodable polymer is poly($\epsilon$-caprolactone) having a melting point below 65° C.

14. A composition as claimed in claim 10, wherein the biocompatible, bioerodable polymer is poly($\epsilon$-caprolactone) having a melting point below 65° C.

15. A composition as claimed in claim 7, wherein hydrolysis of the polymer under physiologic conditions occurs at a rate which does not cause the local pH within the composition to drop below 4.

16. A device for the controlled release delivery of a bioactive peptide or polymer to an animal comprising the composition of claim 1 in the form of a shaped implant.

17. A device for the controlled release delivery of a bioactive peptide or polymer to an animal comprising the composition of claim 7 in the form of a shaped implant.

18. A device as claimed in claim 16, wherein the shaped implant is in a form selected from rods, discs and spheres.

19. A method of controlled release administration of a bioactive peptide or protein to an animal in need of such administration which comprises implanting the device of claim 16 into such animal.

20. A method of controlled release administration of a bioactive peptide or protein to an animal in need of such administration which comprises implanting the device of claim 17 into such animal.

21. A method of controlled release administration of a bioactive peptide or protein to an animal in need of such administration which comprises implanting the device of claim 18 into such animal.

22. A method for producing a composition for the controlled release delivery of a bioactive peptide or protein which comprises (a) dispersing a glassy matrix comprising the bioactive peptide or protein and a thermoprotectant in a biocompatible, bioerodable polymer at a temperature above the melting point of the polymer and below the glass transition temperature of the glassy matrix; and (b) cooling the dispersion to a temperature at which the polymer is a solid.

23. A method as claimed in claim 22, wherein the glassy matrix is in the form of a lyophylized powder.

24. A method as claimed in claim 22, wherein the biocompatible, bioerodable polymer is biodegradable.

25. A method as claimed in claim 22, wherein the glass transition temperature of the glassy matrix phase is above 65° C.

26. A method as claimed in claim 22, wherein the thermoprotectant is selected from the group consisting of trehalose, lactose, maltose, cellobiose, melezitose, melibiose, raffinose and sucrose.

27. A method as claimed in claim 22, wherein the biocompatible, bioerodable polymer is poly($\epsilon$-caprolactone).

28. A method as claimed in claim 22, wherein the bioactive peptide or protein is basic fibroblast growth factor or vascular endothelial growth factor.

29. A method as claimed in claim 28, wherein the thermoprotectant is selected from the group consisting of trehalose, maltose, cellobiose, melezitose, melibiose, raffinose and sucrose.

30. A method as claimed in claim 29, wherein the thermoprotectant is sucrose and the glassy matrix has a moisture content below 0.5%.

31. A method as claimed in claim 28, wherein the thermoprotectant is trehalose.

32. A method as claimed in claim 28, wherein the biocompatible, bioerodable polymer is poly($\epsilon$-caprolactone).

33. A method for alleviating reduced blood flow in an animal due to a vascular blockage which comprises implanting at or near the site of such blockage the drug delivery device of claim 17.

34. A method as claimed in claim 33, wherein said device contains from about 25 $\mu$g to about 250 $\mu$g of bFGF.

35. A method as claimed in claim 33, wherein said animal is a human having coronary artery disease or peripheral vascular disease.

36. A method for promoting wound healing in an animal which comprises applying to a wound an amount of the composition of claim 7 effective for promoting angiogenesis and fibroblast accumulation.

* * * * *